US006229872B1

(12) United States Patent
Amos

(10) Patent No.: US 6,229,872 B1
(45) Date of Patent: May 8, 2001

(54) METHOD AND APPARATUS FOR USE IN INSPECTION OF OBJECTS

(75) Inventor: Jay M. Amos, Hobe Sound, FL (US)

(73) Assignee: United Technologies Corporation, Hartford, CT (US)

( * ) Notice: Subject to any disclaimer, the term of this patent is extended or adjusted under 35 U.S.C. 154(b) by 0 days.

(21) Appl. No.: 09/218,577

(22) Filed: Dec. 22, 1998

(51) Int. Cl.[7] .................................................. G01N 21/00
(52) U.S. Cl. ........................ 378/58; 378/197; 73/622; 356/237.1
(58) Field of Search ............................. 378/57, 59, 58, 378/197; 73/618, 622, 633; 356/237.1

(56) References Cited

U.S. PATENT DOCUMENTS

| Re. 35,423 | * | 1/1997 | Adams et al. | 378/58 |
|---|---|---|---|---|
| 3,778,757 | * | 12/1973 | Houston | 73/626 |
| 4,321,473 | * | 3/1982 | Albert | 378/149 |
| 5,237,598 | * | 8/1993 | Albert | 378/57 |
| 5,745,143 | | 4/1998 | Edgar et al. | 347/139 |
| 5,859,811 | | 1/1999 | Miller et al. | 367/35 |

OTHER PUBLICATIONS

Computer Vision, By Dana Dallard and Chris Brown, Prentice Hall, 1982, pp. 102–105.
Computer Vision, By Dana Dallard and Chris Brown, Prentice Hall, 1982, pp. 196–201.
Reference sheet: X–ray Crystallography, one sheet, May 19, 1996.

* cited by examiner

Primary Examiner—Robert H. Kim
Assistant Examiner—Drew A. Dunn

(57) ABSTRACT

A method and an apparatus generate a plurality of inspection signals each indicative of an internal physical characteristic of a portion of an object. Each of the inspection signals is generated with a different orientation relative to the portion of the object. A signal is generated indicative of a measure of correlation between the inspection signals. The method and the apparatus can be used to reduce the effect of noise and/or distortion in regard to inspection of objects. In one detailed embodiment, the inspection signals are x-ray images indicative of a density of an object. The x-ray images are processed to identify indications in the x-ray images that indicate a density associated with a defect. The indications in the images are then compared to each other to determine whether there is a correlation between the indications. Low correlation between the indications tends to indicate the presence of distortion in the inspection signals. High correlation between the indications indicates lack of distortion in the x-ray images. Such method and the apparatus are used to better distinguish between a portion of an x-ray indicative of distortion and a portion of an x-ray image indicative of defects, in reasonably rapid fashion, thereby making inspection of objects having relatively large, randomly oriented grains economical and practical.

20 Claims, 8 Drawing Sheets

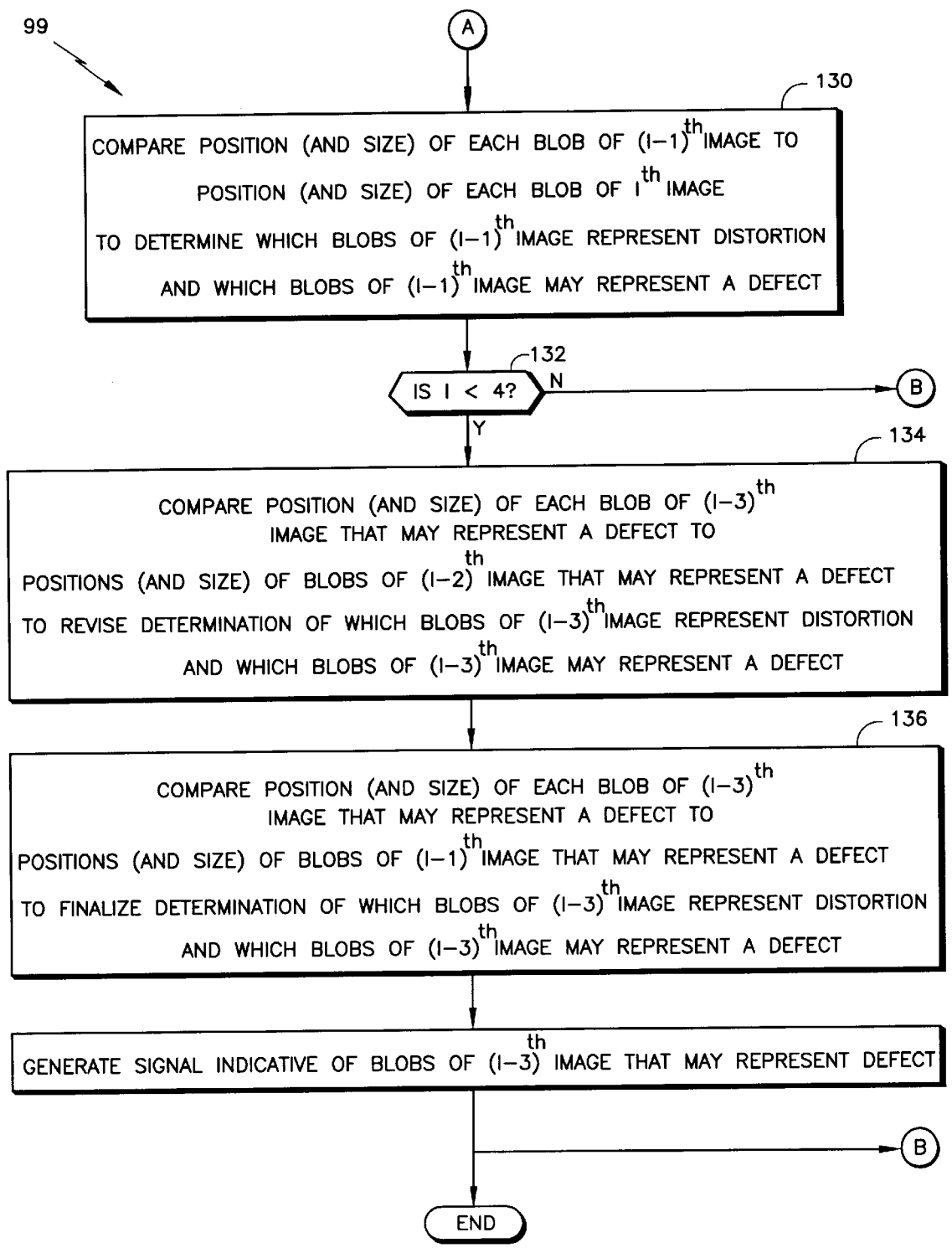

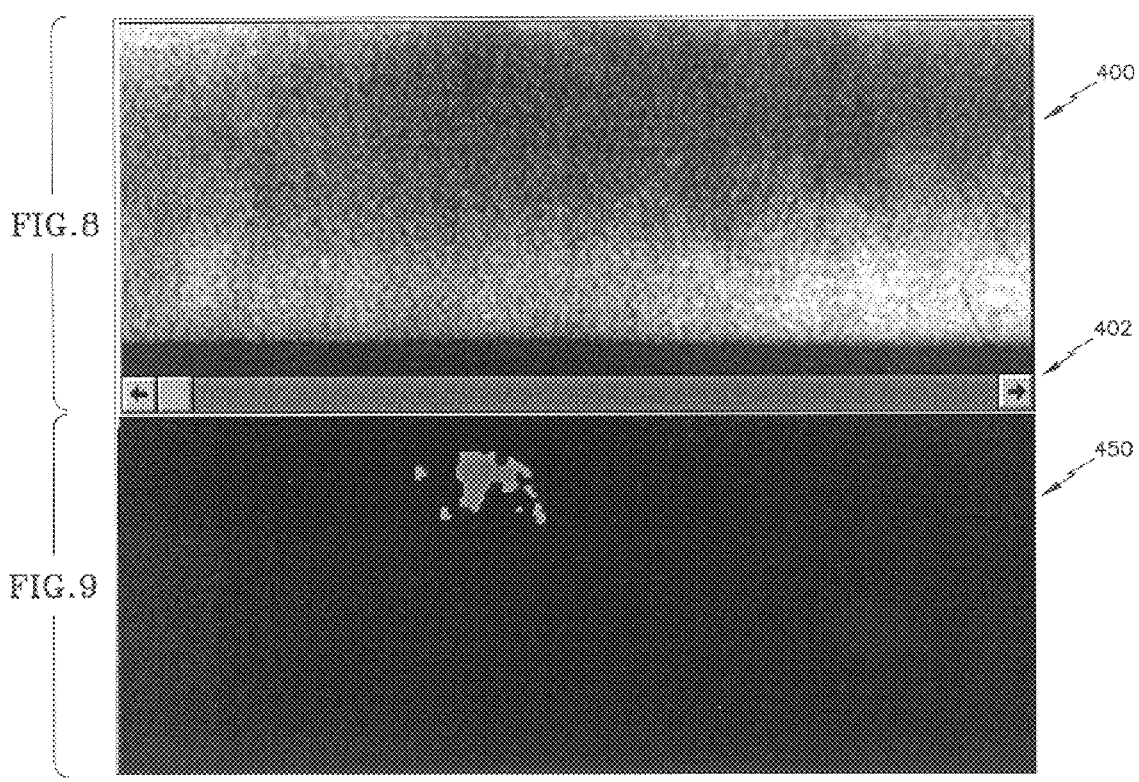

METHOD AND APPARATUS FOR USE IN INSPECTION OF OBJECTS

DESCRIPTION

The U.S. Government has rights relating to this invention pursuant to Air Force Contract F33657-91-C-0007.

TECHNICAL FIELD

The invention relates to a method and an apparatus for use in inspecting an object and more particularly to a method and an apparatus for use in inspecting an object and to help reduce the effect of noise and/or distortion on the results of such inspection.

BACKGROUND ART

Many industries use non-destructive inspection systems to inspect objects. These inspection systems typically generate signals indicative of physical characteristics of the objects. However, there is often noise and/or distortion, collectively referred herein to as distortion, in the signals. The distortion can limit the usefulness of the signals, and thereby hinder the inspection.

For example, many large structural castings (e.g., diffuser cases, liners, etc.) are used in the aerospace and the power generation industries. These castings typically comprise a material having a crystalline microstructure characterized by a plurality of individual crystals, commonly referred to as grains. The grains are often relatively large in size. For example, IN718, a high strength nickel alloy containing Chromium, Cobalt, Titanium, and Aluminum, has grains of sizes in the range of from about 0.060 inches to about 0.180 inches. The grains are generally randomly oriented throughout the casting.

The castings sometimes contain internal defects such as microshrinkage, cracks, and inclusions. These defects are all characterized by a relatively low density and are accordingly referred to as low-density defects. Some of these defects may be subtle in that they are relatively small in size and/or may have only slightly different density than that of regions surrounding the defect. For example, a microshrinkage defect is a region characterized by clusters of slight porosity in the microstructure resulting in slightly lower density than that of surrounding regions. However, even a subtle defect can be significant enough to effect the reliability of the casting.

Radiographic inspection systems have typically been used to try to detect internal defects in the castings. Radiographic inspection systems pass x-rays through an object to produce x-ray photographs (i.e., x-ray images) indicative of physical characteristics of the object.

However, the relatively large, generally randomly oriented grains in the microstructure cause a significant amount of unwanted scattering and diffraction of the x-rays as they pass through the casting. Consequently, the x-ray images contain a high level of distortion. The distortion is in the form of intensity variation (sometimes referred to as mottling). The intensity variation associated with the distortion is often greater in magnitude than intensity variation associated with some subtle but significant defects. Hence, the distortion makes it difficult or impossible to determine that there are no subtle but significant defects by means of conventional inspection of the x-ray images. For instance, it has traditionally not been possible to detect a 0.100 inch long microshrinkage defect in a nickel casting having a wall thickness of 0.250 inches on the basis of a conventional x-ray image.

Due to such distortion, some subtle but significant defects sometimes go undetected until discovered during machining of the casting. In the event that the casting is defective and must be scrapped, time and effort devoted to machining is wasted. On the other hand, the distortion sometimes results in a false positive, i.e., identifying, as a defect, a feature that is not a defect. At the very least, false positives require an investigation, which can be time consuming. False positives can, even after investigation, result in a satisfactory casting being rejected as though it is defective one, thereby impacting production costs.

Various methods currently exist to help evaluate an x-ray image, e.g., contrast stretching, shift subtraction, sharpening, and/or filtering. These methods have been useful in radiographic inspection systems for objects that do not have large grains, for example fine-grained airfoils and microelectronics. None of these methods are effective for detecting relatively subtle but significant defects based on an x-ray image having a high level of distortion from large grains.

SUMMARY OF THE INVENTION

An object of the present invention is to provide a method and an apparatus for use in inspecting an object to help reduce the effect of distortion.

The present invention is predicated, in part, on the recognition that although there may be distortion in a signal generated by an inspection system in regard to an internal physical characteristic of a portion of an object, in many situations the distortion is a function of the relative orientation between the inspection system and the portion of the object, and that such distortion may be identified by changing the relative orientation, generating another signal indicative of the internal physical characteristic of the portion of the object, and determining a measure of correlation between the signals. Lack of correlation between the signals tends to indicate the presence of distortion in one or both of the signals.

According to the present invention a method and an apparatus for use in inspecting an object generate a plurality of inspection signals each indicative of at least one internal physical characteristic of a portion of the object, wherein each of the inspection signals is generated from a different orientation relative to the portion of the object, and generate a signal indicative of at least one measure of correlation between the plurality of inspection signals.

The present invention can be used to reduce the effect of distortion in regard to inspection of objects. In one detailed embodiment, the invention is used to better distinguish between an x-ray indicative of distortion and an x-ray image indicative of defects, in reasonably rapid fashion, thereby making inspection of objects having relatively large, randomly oriented grains economical and practical.

These and other objects, features and advantages of the present invention will become more apparent in the light of the following detailed description, accompanying drawings, and claims.

BRIEF DESCRIPTION OF THE DRAWINGS

FIG. 5, including FIGS. 5A and 5B, is a flowchart of steps in a program executed by the inspection system of FIG. 3;

FIG. 6 is an output image produced by the inspection system of FIG. 3 in response to the x-ray image of FIG. 1;

FIG. 8 is an x-ray image of an object to be inspected by the inspection system of FIG. 3;

FIG. 9 is an output image produced by the inspection system of FIG. 3 in response to the x-ray image of FIG. 8;

BEST MODE EMBODIMENT FOR CARRYING OUT THE INVENTION

To illustrate the problem associated with radiographic inspection of the large structural castings described above, FIG. 1 is an x-ray image of a first object (not shown) having a microstructure with relatively large, generally randomly oriented grains. The x-ray image 20 has a high level of intensity variation that serves as an example of intensity variation that often results in an x-ray image of such a microstructure. In the absence of distortion, a relatively darker region in an x-ray image typically represents a region in an object that has a relatively lower density than that of surrounding regions. Thus, a relatively darker region may be indicative of a low density defect. Although the x-ray image has many relatively darker regions, e.g., regions 22A–22G, the first object has no significant defects. All of the relatively darker regions 22A–22G (and for that matter, all the relatively lighter regions) represent distortion caused by the grains in the microstructure of the object. However, the distortion makes it difficult to confirm the absence of any subtle but significant defects based on inspection of the x-ray image 20.

Figures 2, 7:
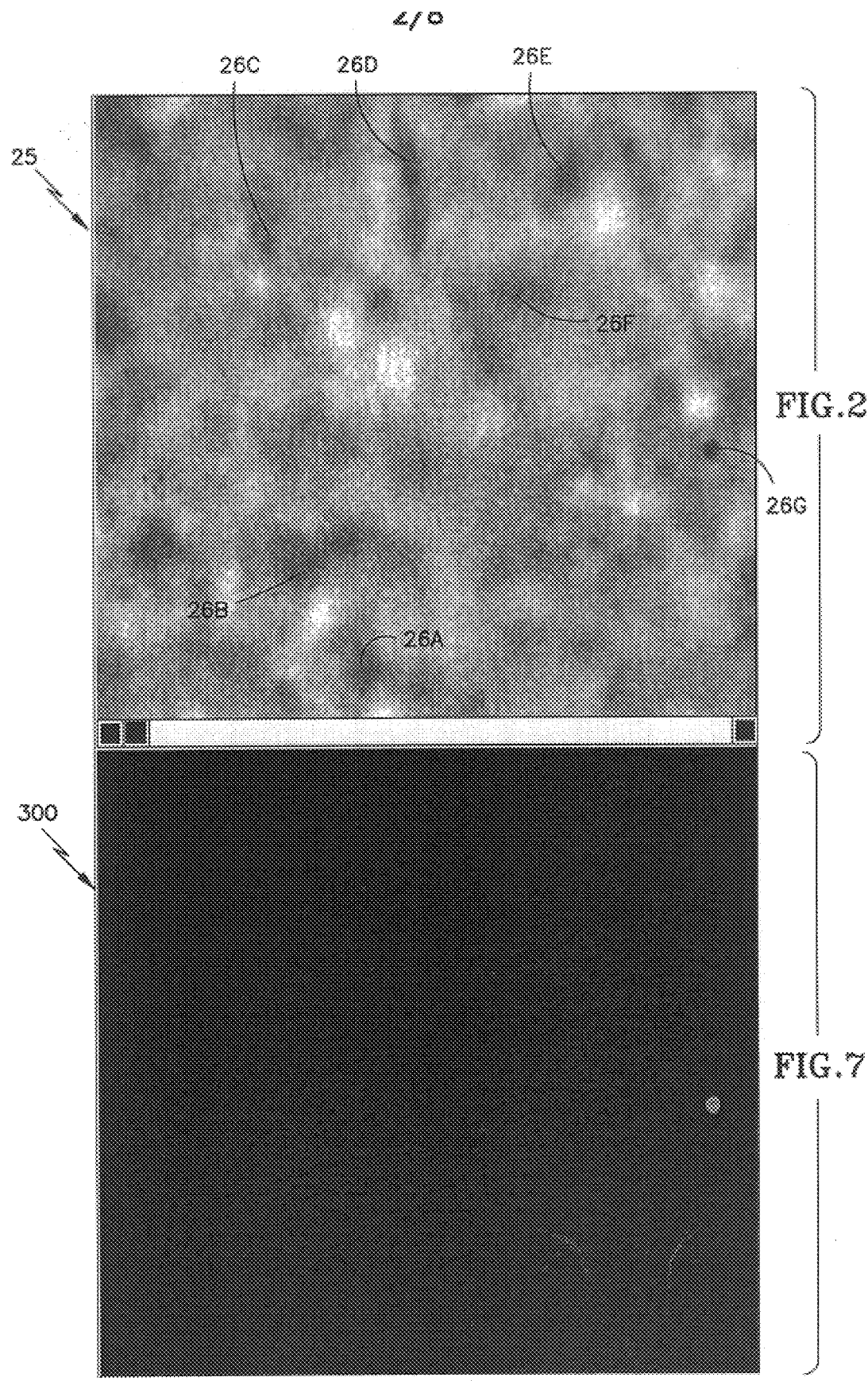
FIG. 2 is an x-ray image of a second object having a relatively large grain microstructure.
FIG. 7 is an output image produced by the inspection system of FIG. 3 in response to the x-ray image of FIG. 2.

Referring now to FIG. 2, an x-ray image 25 of a second object (not shown) having relatively large, generally randomly oriented grains serves as another example of intensity variations (e.g., distortion) that often result from such a microstructure. Although the x-ray image 25 has many relatively darker regions, e.g., regions 26A–26G, the second object has only one defect. The defect is represented in the image by the relatively darker region 26G. It is relatively easy to determine the presence of the defect based on the x-ray image 25 because the density of the defect is more than slightly different than that of surrounding regions. This is because the defect is a void rather than a more subtle defect. All of the other relatively darker regions 26A–26F represent distortion caused by the grains in the microstructure of the object. However, the distortion makes it difficult to confirm the absence of any subtle but significant defects based on inspection of the x-ray image 25.

It has been determined that distortion in an x-ray image for an object having relatively large, generally randomly oriented grains greatly depends on the relative orientation between the inspection system and the object. One reason for this is that the distortion is a consequence of x-ray scattering and diffraction, which are orientation dependent. Another reason is that the grains, which cause the scattering and the diffraction, are generally randomly oriented. In contrast, the x-ray image of many types of defects generally does not depend on the relative orientation between the inspection system and the object, particularly for small changes in orientation. This is primarily because the image is a consequence of attenuation (or lack thereof) of the x-rays. Such attenuation is not significantly dependent on orientation.

To this effect, and in view of the description below, it will be understood that in the best mode embodiment described hereinbelow, the present invention generates a plurality of x-ray images indicative of the density of a portion of an object having relatively large grains. Each of the inspection signals is generated from a different orientation relative to the portion of the object. The x-ray images are processed to identify any indications in the x-ray images that indicate a density associated with a low density defect. The indications are then compared to each other to determine whether there is a correlation between the indications. Low correlation between the indications tends to indicate distortion in x-ray images. High correlation indicates lack of distortion in the x-ray images.

Figure 3:
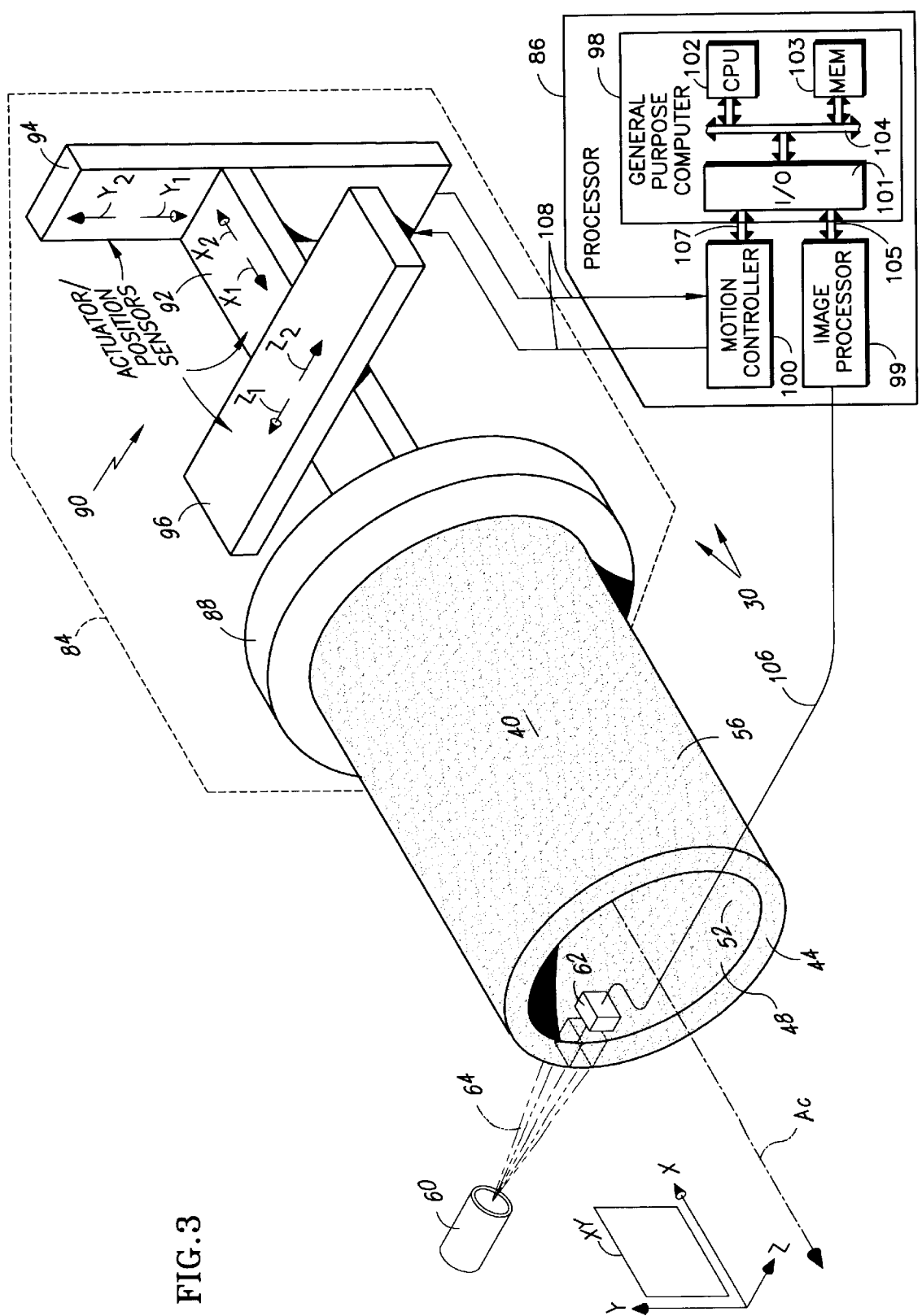
FIG. 3 is a perspective view of a diffuser case for a gas turbine engine, in combination with a representation of an inspection system according to a best mode embodiment of the present invention.

The present invention is disclosed with respect to a best mode embodiment for use in a real time x-ray inspection system 30 used to detect defects in a diffuser case 40 for a gas turbine engine, as illustrated in FIG. 3. The diffuser case 40 is one type of large structural casting. The diffuser case 40 has a cylindrical wall 44 and a hollow interior 48 disposed about a central axis $A_c$. The wall 44 has an inner surface 52 and an outer surface 56. The wall 44 comprises a material having a crystalline microstructure with relatively large, generally randomly oriented grains. For example, the wall material may comprise a high strength nickel alloy. The surface and/or microstructure of the wall 44 could have any of various types of defects, including, but not limited to, microshrinkage, cracks and inclusions.

The real time inspection system 30 has mutually orthogonal reference axes including: an x axis, X, a y axis, Y, and a z axis, Z. The x axis of the inspection system 30 is parallel to the central axis $A_c$ of the diffuser case 40. The x axis and the y axis are disposed within an xy plane, XY.

The real time inspection system 30 includes an x-ray source 60 and an x-ray detector 62. The x-ray source 60 may be positioned about thirty inches from the outer surface 56 of the diffuser case 40. The x-ray detector 62 may be disposed in the hollow interior 48 of the diffuser case 40. The x-ray source generates a source x-ray signal 64, which is directed toward the outer surface 56 of the diffuser case 40, preferably in a direction parallel to the z axis. The source x-ray signal 64 has a relatively small spot size, e.g., about twelve microns. The relatively small spot size facilitates use of a detector having geometric magnification. The source x-ray signal 64 has a relatively high energy (e.g., about 225 kiloelectron volts), which is selected in view of the density and thickness of the diffuser case 40. The relatively high energy ensures that some of the x-rays have sufficient energy to pass completely through the wall of the diffuser.

Figure 4:
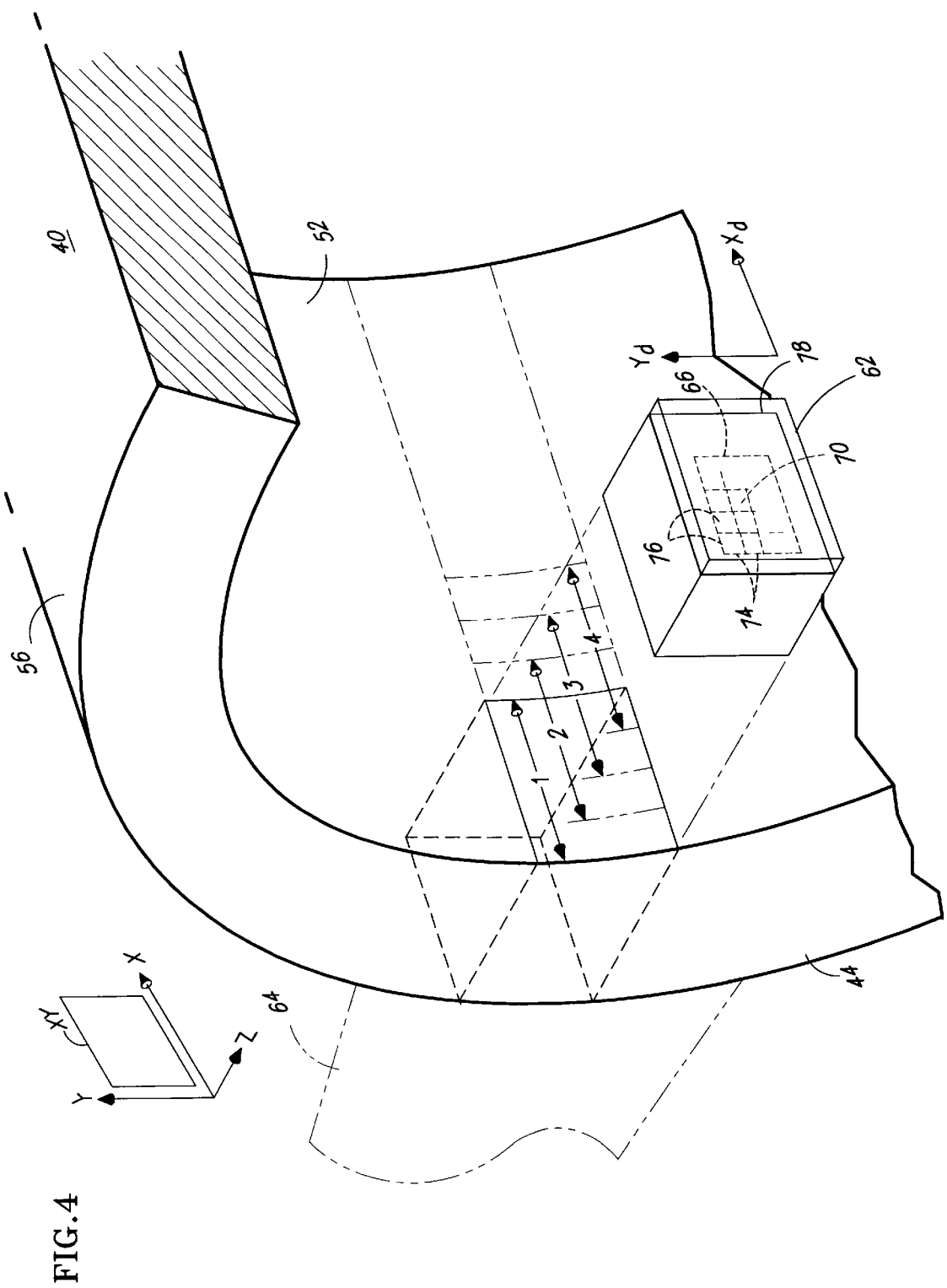
FIG. 4 is an enlarged perspective view of a portion of the casting of FIG. 3 in combination with an enlarged representation of a source signal and a detector of the inspection system of FIG. 3.

The x-ray detector 62 includes an x-ray conversion screen (not shown) and a digital detector having a detector array 66 (FIG. 4). The detector array 66 is preferably a device with relatively high resolution and relatively large dimensions (e.g., at least about four inches by about four inches) to facilitate direct imaging of x-rays and reasonably high inspection rates. An x-ray detector 62 of this type is commercially available, e.g., a series LAST amorphous silicon detector manufactured by Varian.

Referring now to FIG. 4, in an enlarged view of the x-ray detector 62 and a portion of the diffuser case 40, the detector array 66 has a plurality of detector elements, represented by a detector element 70. The detector elements are disposed generally within a plane 78, referred to herein as the detector plane 78. The detector array has orthogonal detector reference axes, including an axis, $X_d$ and an axis, $Y_d$, which are disposed in the detector plane 78. The detector elements 70 are arranged in a plurality of rows, represented by rows 74, and a plurality of columns, represented by columns 76, that run parallel to the detector reference axes. The x-ray detector 62 is oriented so as to have the detector plane 78 parallel to the xy plane XY. The detector elements 70 are directed toward the inner surface 52 of the wall 44 of the diffuser case 40. The x-ray detector 62 has a field of view corresponding to an expanse viewable by the detector array 66. Each of the detector elements 70 views a respective portion of the field of view.

Referring again to FIG. 3, the inspection system 30 further includes a manipulator 84 and a processor 86. The manipulator is used to position the diffuser case 40. The manipulator 84 includes a turntable 88 and a plurality of actuators/sensors 90. The turntable supports the diffuser case 40 and provides rotational positioning about the x axis. The plurality of actuators/sensors 90 includes a first actuator/sensor 92, a second actuator/sensor 94, and a third actuator/sensor 96. The first actuator/sensor 92 provides positioning in directions $x_1$, $x_2$ parallel to the x axis. The second actuator/sensor 94 provides positioning in directions $y_1$, $Y_2$ parallel to the y axis. The third actuator/sensor 96 provides positioning in directions $z_1$, $z_2$ parallel to the z axis. In addition, the plurality of actuators/sensors 90 provide position signals indicative of their respective positioning.

The processor 86 comprises a general purpose industrial computer 98, an image processor 99, and a motion controller 100. The general purpose computer 98 has an input/output (I/O) portion 101, a central processing unit portion (CPU) 102, a memory portion 103, and a bus portion 104 with connections to each of the other portions 101, 102, 103. The image processor 99 is a commercially available type that includes an image processing board (not shown) with a frame grabber, an image memory, and a co-processing module. The general purpose industrial computer 98 is electrically connected to the image processor 99 via a plurality of signal lines 105. The image processor 99 is electrically connected to the x-ray detector 62 via a plurality of signal lines, represented by a signal line 106. The general purpose computer is electrically connected to the motion controller 100 via a plurality of signal lines 107. The motion controller 100 is electrically connected to the manipulator 84 via a plurality of signal lines, represented by signal lines 108.

The processor 86 further includes a program stored in the memory portion 103 of the general purpose computer 98. The program may comprise a series of modules in software or firmware having a series of instructions or steps (FIG. 5) to be executed by the CPU portion 102 of the general purpose computer 98. The program is described in further detail hereinbelow with respect to FIGS. 4, 5.

Figure 5A:
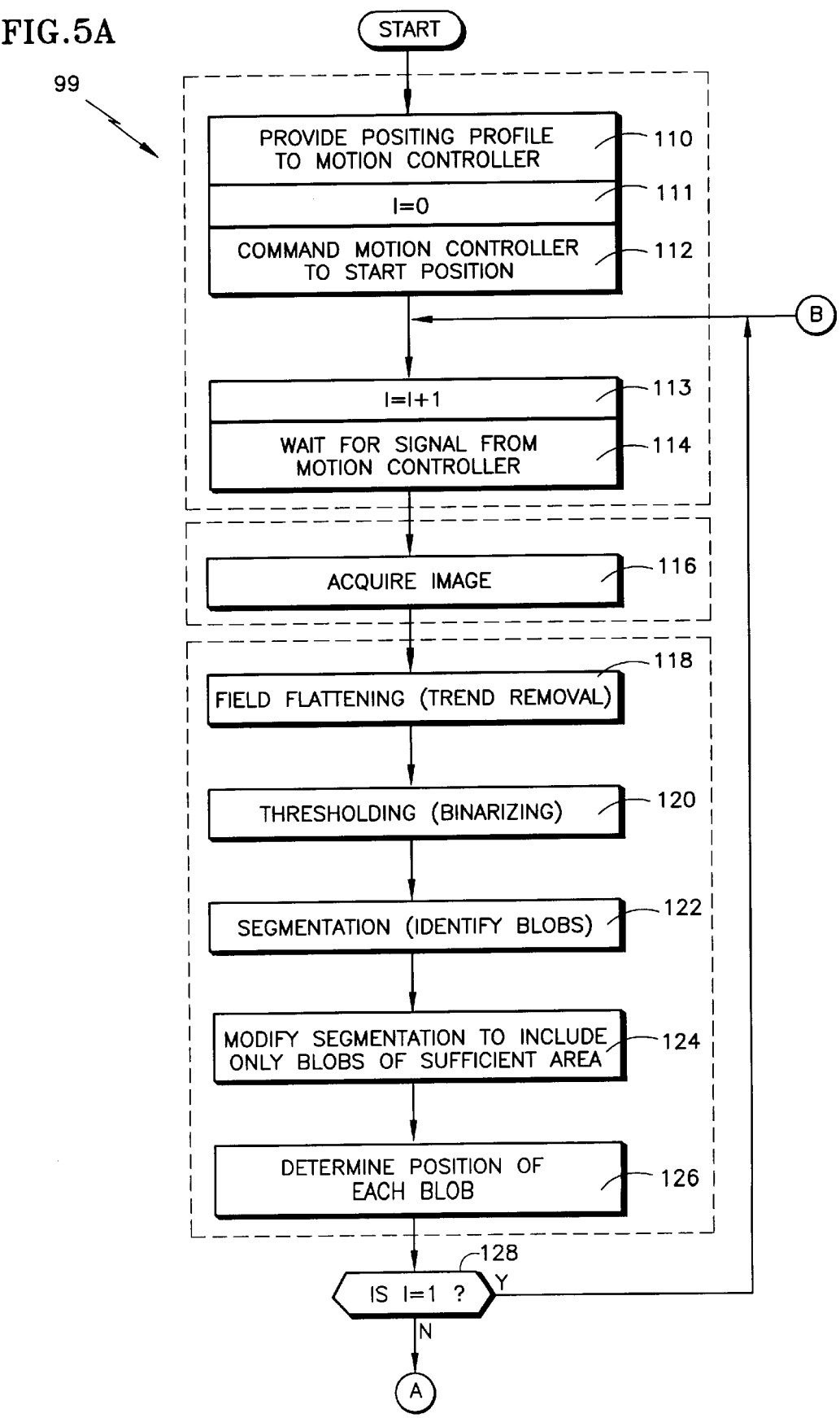

Operation of the inspection system 30 is described with respect to FIG. 4 and with respect to FIG. 5 (including FIGS. 5A and 5B), a flowchart 109 of the steps in the program stored and executed in the general purpose computer 98 of the processor 86. Referring now to FIGS. 4, 5, at an initial step 110 in the program, the general purpose computer 98 provides initialization signals to the motion controller 100. The initialization signals are indicative of positioning sought for the diffuser case, which depends on the relative positioning sought between the diffuser case 40, the x-ray source 60 and the x-ray detector 62. In one embodiment, the positioning signals to the motion controller 100 indicate a first position for which an image is sought, an amount of positional change sought between image acquisitions, a rate of change of position (velocity), and an ending position. At a step 111, the general purpose computer sets the magnitude of an image counter signal, I, equal to zero.

At a step 112, the general purpose computer 98 of the processor 86 initiates positioning by providing a signal commanding the motion controller 100 to "start". In response, the motion controller 100 provides control signals on signal lines 108 that cause the manipulator 84 to move the diffuser case 40 toward the first position. At a step 113, the general purpose computer increments the magnitude of the image counter signal, I, by one. The processor 86 waits at a step 114 for a signal on signal lines 107 from the motion controller 100 indicating that the diffuser case 40 has reached the first position.

With the diffuser case 40 at the first position, the inspection system 30 is in position to generate an x-ray image for a first portion of the diffuser case. The x-ray source 60 generates a source x-ray signal 64 that strikes the outer surface of the first portion of the diffuser case. Some of the x-rays from the source x-ray signal are transmitted through (i.e., pass completely through) the first portion and result in an output x-ray signal that exits the first portion by way of the inner surface. The output x-ray signal is indicative of the density characteristics of the first portion of the diffuser case 40. The signal may also have distortion brought about by the relatively large, randomly oriented grains in the microstructure of the diffuser case 40.

The output x-ray signal is detected by the detector array 66 of the x-ray detector 62. Specifically, each detector element 70 detects a portion of the output x-ray signal that is within its portion of the field of view. The x-ray detector 62 generates an inspection signal in response thereto. The inspection signal represents a two dimensional, x-ray image for the first portion of the diffuser case. The x-ray image 20 (FIG. 1) and the x-ray image 25 (FIG. 2) are examples of two dimensional, x-ray images.

An x-ray image can be viewed as having a plurality of locations each having a picture intensity. The picture intensity at each location is a function of the portion of the output signal detected by one of the detector elements, and therein is indicative of the density characteristics of the portion of the diffuser case.

The inspection signal is typically of a type that represents the image as a plurality of picture element (pixel) magnitudes. Each pixel magnitude indicates the picture intensity (relative darkness or relative lightness) at an associated location of the image. A relatively low pixel magnitude indicates a relatively low picture intensity (i.e., relatively dark location). Conversely, a relatively high pixel magnitude indicates a relatively high picture intensity (i.e., relatively light location). The pixel magnitudes are selected from a range that depends on the resolution of the x-ray detector. For example, a range of from 0 to 255 is used for an 8 bit detector.

At a step 116, the general purpose computer 98 provides a control signal on signal lines that direct the image processor 99 to acquire an inspection signal from the x-ray detector 62. Subsequent steps comprise a series of image processing steps, described in further detail below, to detect indications of the x-ray image that are potentially indicative of a low density defect in the first portion of the diffuser case 40. In executing these steps, the general purpose computer 98 provides control signals to the image processor 99 indicative of basic image processing tasks. The image processor 99 implements the basic image processing tasks faster than a typical general purpose computer 98. On completion, the image processor 99 provides data signals back to the general purpose computer 98.

At a step 118, the processor 86 initiates a field flattening operation (sometimes referred to as a trend removal operation) on the inspection signal to generate a field flattened image signal. Field flattening is well known in image processing and may be considered somewhat analogous to high pass filtering. In this instance, field flattening removes effects of minor variations in the thickness of the diffuser case 40 and non-uniformities introduced by the x-ray detector 62.

At a step 120, the processor 86 initiates a thresholding operation on the field flattened image signal to generate a thresholded image signal. Thresholding is well known in image processing. In the thresholding operation, the processor compares the pixel magnitude of each location in the field flattened image signal to a reference magnitude. For instance, the reference magnitude is chosen to correspond to a pixel magnitude indicative of a density associated with a low density defect. If a pixel magnitude for a location in the field flattened image is lower than the reference magnitude, the processor generates a maximum pixel magnitude (e.g., 255) for the corresponding location in the thresholded image signal. Otherwise the processor generates a minimum pixel magnitude (e.g., 0) for the corresponding location in the thresholded image signal. With this convention, a minimum pixel magnitude in the thresholded image signal indicates a density associated with a suitable density. A maximum pixel magnitude indicates a density associated with a low density defect.

The thresholded image signal generated as described above represents a thresholded image. The thresholded image has a dark background, which is desirable for most image processing routines. Locations with a high picture intensity (i.e., light locations) in the thresholded image indicate a density associated with a low density defect.

At a step 122, the processor 86 initiates a segmentation operation. Segmentation is well known in image processing. In the segmentation operation, the processor identifies indications in the thresholded image signal that indicate a density associated with a low density defect. This is accomplished by identifying blobs in the thresholded image signal. In image processing, a blob typically represents a light feature in an image and is characterized by a group of pixel magnitudes that are equal to the maximum pixel magnitude and associated with contiguous locations in the image. The processor generates a segmentation signal indicative of the results.

The inspection system 30 is concerned with defects of at least a certain size. Consequently, at a step 124, the processor 86 determines which of the blobs is large enough in size to be indicative of a defect of at least the certain size. To make this determination, the processor 86 computes an area for each blob and compares the area to a reference magnitude. If the area is less than the reference magnitude, then that blob does not represent a defect of at least the certain size. Otherwise the blob does potentially represent a defect of at least a certain area. Only the blobs representing a large enough region are used in further processing. This step helps to reduce the amount of processing required at subsequent steps in the program.

At a step 126, the processor 86 computes a position for each of the blobs identified in the step 124, and further generates a blob position signal indicative thereof. Any suitable convention for determining and/or specifying the positions of the blobs may be used. In a preferred embodiment, the processor 86 determines a centroid (which is well known in the art) for each of the blobs. The processor 86 then determines an image position and/or a corresponding diffuser case 40 position for each of the centroids, and uses these positions to represent the positions of the blobs.

At a step 128, the processor 86 determines whether this is the first image in a scan path. If so, execution reverts back to the step 114, where the processor 86 waits for a signal from the motion controller 100 indicating that the diffuser case 40 has reached a second position. The scan path is preferably parallel to the detector plane 78 and more preferably parallel to one of the detector reference axes (i.e., axis $X_d$ and axis $Y_d$) to simplify processing steps below.

At the second position, the diffuser case 40 has a second positional relation to the x-ray source 60 and/or the x-ray detector 62, and the x-ray detector 62 has a second portion 50 of the diffuser case 40 within its field of view. The second portion overlaps the first portion, thereby defining an overlap portion. The width of the overlap portion represents a compromise between inspection throughput and effectiveness at determining the presence of distortion. The overlap width is typically at least 0.5 times that of the first portion, so that every indication (e.g., blob) of an x-ray image that is potentially indicative of a defect will fall into at least one overlap portion. This results in one opportunity to determine which of the indications (e.g., blobs) represent true defects. An overlap width of 0.66 times that of the first portion, results in two opportunities to determine which of the indications (e.g., blobs) of the x-ray image represent distortion. In the present embodiment, the width is about 0.75 times that of the first portion, which results in three opportunities to determine which of the indications (e.g., blobs) of the x-ray image represent distortion, yet does not excessively extend the inspection time. With such overlap, the distance between the first and the second positions may be relatively small in magnitude, for example, representing an angular displacement of 1 or 2 degrees between the x-ray detector 62 and the first portion of the diffuser case 40.

Much of the translation from the first position to the second position preferably occurs concurrent with execution of the steps above. The rate of change in position (i.e., velocity) is preferably slow enough that it does not hinder acquisition of accurate images (a digital detector can typically provide an image about every 1/30 seconds) and results in enough time for the processor 86 to finish processing the image from one position before reaching the next position for which an image is sought. For example, in one embodiment, the field of view of the x-ray detector 62 is six inches, the time needed for processing is 2 seconds, the positional change sought between image acquisitions is ¼ of the field of view (i.e., 1.5 inches), and the velocity is 0.5 inches/second.

The x-ray source 60 generates a source x-ray signal 64 that results in an output x-ray signal at the x-ray detector 62, which in turn provides an inspection signal, indicative of a two dimensional x-ray image of the second portion of the diffuser case 40. The processor 86 re-executes steps 116–126 to process the signal for the second portion in a manner similar to that provided for the first portion, described above.

Subsequent steps described hereinbelow are aimed at determining which of the indications (e.g., blobs) of the x-ray images represent distortion, and which represent a defect in the diffuser case 40. This is accomplished by determining whether there is a measure of correlation between x-ray images for two or more overlapping portions. Low correlation between the indications tends to indicate distortion in x-ray images. High correlation between the indications indicates lack of distortion in the x-ray images. At a step 130, the processor 86 makes an initial determination as to whether the blobs in the first image represent distortion or whether they may represent a defect. The processor 86 makes a separate determination for each of the blobs in the first image. To make the determination for a particular blob in the first image, the processor 86 determines whether there is sufficient correlation (e.g., in position and/or size) between the blob in the first image and any of the blobs in the second image. The processor may employ test (1) and test (2) below as a measure of the correlation:

$$\text{PosDiff}_{tol} > |(\text{Pos}_{blob\ 1st\ image} + \text{PosDiff}_{oriented\ 1st\ image\ to\ orient\ 2nd\ image}) - \text{Pos}_{blob\ 2nd\ image}| \quad \text{(test 1)}$$

$$\text{SizeDiff}_{tol} > |\text{Size}_{blob\ 1st\ image} - \text{Size}_{blob\ 2nd\ image}| \quad \text{(test 2)}$$

where $\text{PosDiff}_{tol}$ is a tolerance magnitude for a position difference, $\text{Pos}_{blob\ 1st\ image}$ is the position of the blob in the first image, $\text{PosDiff}_{orient\ 1st\ image\ to\ orient\ 2nd\ image}$ is the position difference introduced by the difference between the relative orientation of the diffuser case/source/detector for the first image and the relative orientation of the diffuser case/source/detector for the second image, $\text{Pos}_{blob\ 2nd\ image}$ is the position of a blob in the second image, $\text{SizeDiff}_{tol}$ is a tolerance magnitude for a size difference, $\text{Size}_{blob\ 1st\ image}$ is the size of the blob in the first image, $\text{Size}_{blob\ 2nd\ image}$ is the size of the blob in the second image.

The tolerance magnitude for the size difference, $\text{SizeDiff}_{tol}$, may for example be 20% of the size of the blob in the first image. Note that a change in position is typically a vector having a magnitude component and a direction component, computed using classical vector mathematics. $\text{PosDiff}_{tol}$ may for example be 10% of the magnitude of the $\text{PosDiff}_{orient\ 1st\ image\ to\ orient\ 2nd\ image}$ and 6% of the direction of the $\text{PosDiff}_{orient\ 1st\ image\ to\ orient\ 2nd\ image}$. In one alternative, two differences may be computed, a difference between an x axis coordinate for the blob in the first image and an x axis coordinates for the blobs in the second image, and a difference between a y axis coordinate for the blob in the first image and an y axis coordinates for the blob in the second image. In such alternative, $\text{PosDiff}_{tol}$ has an appropriate tolerance for the difference along the x axis and an appropriate tolerance for the difference along the y axis. In any case, the tolerances are typically determined empirically and are dependant upon accuracy of the manipulator and properties of the object. A preferred procedure for determining the tolerances employs one or more calibration objects having a defect, of known size and density, similar to that sought to detect with the inspection system 30. Calibration objects without defects may also be employed. Reference magnitudes are set so as to satisfactorily indicate the defects without excessive false positives.

If test (1) and test (2) are true in regard to a particular blob in the second image, then there is a sufficient correlation between the blob in the first image and the particular blob in the second image. Otherwise, there is not sufficient correlation between the blob in the first image and any of the blobs in the second image. The blobs in the first image that have sufficient correlation to a blob in the second image may represent a defect in the diffuser case 40. The blobs in the first image that do not have sufficient correlation to any blob in the second image represent distortion.

The above equations may be generalized as follows:

$$\text{PosDiff}_{tol} > |\text{Pos}_{blob\ Jth\ image} + \text{PosDiff}_{orient\ Jth\ image\ to\ orient\ Kth\ image}) - \text{Pos}_{blob\ Kth\ image}| \quad \text{(test 3)}$$

$$\text{SizeDiff}_{tol} > |\text{Size}_{blob\ Jth\ image} - \text{Size}_{blob\ Kth\ image}| \quad \text{(test 4)}$$

where $\text{PosDiff}_{tol}$ is a tolerance magnitude for a position difference, $\text{Pos}_{blob\ Jth\ image}$ is the position of the blob in the Jth image, $\text{PosDiff}_{orient\ Jth\ image\ to\ orient\ Kth\ image}$ is a position difference introduced by the difference between the relative orientation of the diffuser case/source/detector for the Jth image and the relative orientation of the diffuser case/source/detector for the Kth image, $\text{Pos}_{blob\ Kth\ image}$ is the position of the blob in the Kth image, $\text{SizeDiff}_{tol}$ is a tolerance magnitude for a size difference, $\text{Size}_{blob\ Jth\ image}$ is the size of the blob in the Jth image, $\text{Size}_{blob\ Kth\ image}$ is the size of the blob in the Kth image.

At a step 132 the processor 86 determines that less than four images have been obtained and execution again reverts back to the step 114. At the step 114, the processor 86 waits for a signal from the motion controller 100 indicating that the diffuser case 40 has reached the third position.

At the third position, the diffuser case 40 has a third positional relation to the x-ray source 60 and/or the x-ray detector 62, and the x-ray detector 62 has a third portion 50 of the diffuser case 40 within its field of view. The third portion overlaps the second portion. The x-ray source 60 generates a source x-ray signal 64 that results in an output x-ray signal at the x-ray detector 62, which in turn provides an inspection signal indicative of a two dimensional x-ray image of the third portion of the diffuser case 40. The processor 86 re-executes steps 116–126 to process the signal for the third portion in a manner similar to that provided for the first portion, described above. The processor 86 re-executes step 130 with respect to the second and third portions to make an initial determination as to whether the blobs in the second image represent distortion or whether they may represent a defect, in a manner similar to that described above with respect to the first and second portions and the initial determination as to whether the blobs in the first image represent distortion or whether they may represent a defect. The processor may employ test (3) and test (4) above as a measure of the correlation, where the Jth image is the second image and the Kth image is the third image.

At the step 132 the processor 86 again determines that less than four images have been obtained and execution again reverts back to the step 114. At the step 114, the processor 86 waits for a signal from the motion controller 100 indicating that the diffuser case 40 has reached the fourth position.

At the fourth position, the diffuser case 40 has a fourth positional relation to the x-ray source 60 and/or the x-ray detector 62, and the x-ray detector 62 has a fourth portion 50 of the diffuser case 40 within its field of view. The fourth portion preferably overlaps the first, second, and third portions. The x-ray source 60 generates a source x-ray signal 64 that results in an output x-ray signal at the x-ray detector 62, which in turn provides an inspection signal indicative of a two dimensional x-ray image of the fourth portion of the diffuser case 40. The processor 86 re-executes steps 116–126 to process the signal for the fourth portion in a manner similar to that provided for the first portion, described above. The processor 86 re-executes step 130 with respect to the third and the fourth portions to make an initial determination as to whether the blobs in the third image represent distortion or whether they may represent a defect, in a manner similar to that described above with respect to the first and second portions and the initial determination as to whether the blobs in the first image represent distortion or whether they may represent a defect. The processor may employ test (3) and test (4) above as a measure of the correlation, where the Jth image is the third image and the Kth image is the fourth image.

At the step 132 the processor 86 determines that four images have been obtained and execution passes to a step 134. At the step 134, the processor 86 makes a revised determination as to whether the blobs in the first image represent distortion or whether they may represent a defect. The processor 86 makes a separate revised determination for each of the blobs in the first image that have not already been determined to represent distortion. To make the revised determination for a particular blob in the first image, the processor 86 determines whether or not there is sufficient correlation (e.g., in position and/or size) between the blob in the first image and any of the blobs in the second image that have not already been determined to represent a distortion. The processor may employ test (3) and test (4) above as a measure of the correlation, where the Jth image is the first image and the Kth image is the second image.

At the step 136, the processor 86 makes a final determination as to whether the blobs in the first image represent distortion or whether they may represent a defect. The processor 86 makes a separate final determination for each of the blobs in the first image that have not already been determined to represent distortion. To make the final determination for a particular blob in the first image, the processor 86 determines whether or not there is sufficient correlation (e.g., in position and/or size) between the blob in the first image and any of the blobs in the third image that have not already been determined to represent a distortion. The processor may employ test (3) and test (4) above as a measure of the correlation, where the Jth image is the first image and the Kth image is the third image.

This process continues across the entire scan path. The turntable 88 translates the diffuser casing 40, and inspection proceeds along a second scan path, parallel to the first scan path, in manner similar to that described above for the first scan path. The magnitude of the translation is preferably just slightly less than the height of the portions, thereby ensuring complete inspection yet helping to minimize the inspection time. The process may continue until the critical areas and/or substantially all of the diffuser case 40 has been inspected. As used herein substantially all refers to at least eighty percent of the diffuser case 40.

The processor 86 generates a signal indicative of the results of the steps above. The signal is preferably indicative of the internal physical characteristics of the diffuser case 40 and absent the detected distortion. For example, the output signal may indicate only the indications (e.g. blobs) of the x-ray image that are potentially indicative of a defect. The output signal may provide this information in any of various ways. In the preferred embodiment, the output signal comprises an image signal indicative of a two dimensional image. The image preferably comprises a dark background; relatively lighter regions in the image indicate relatively lower density regions in the diffuser case 40. As a further example, the output signal may alternatively or additionally indicate potential defects by their position, size and shape.

Figure 1:
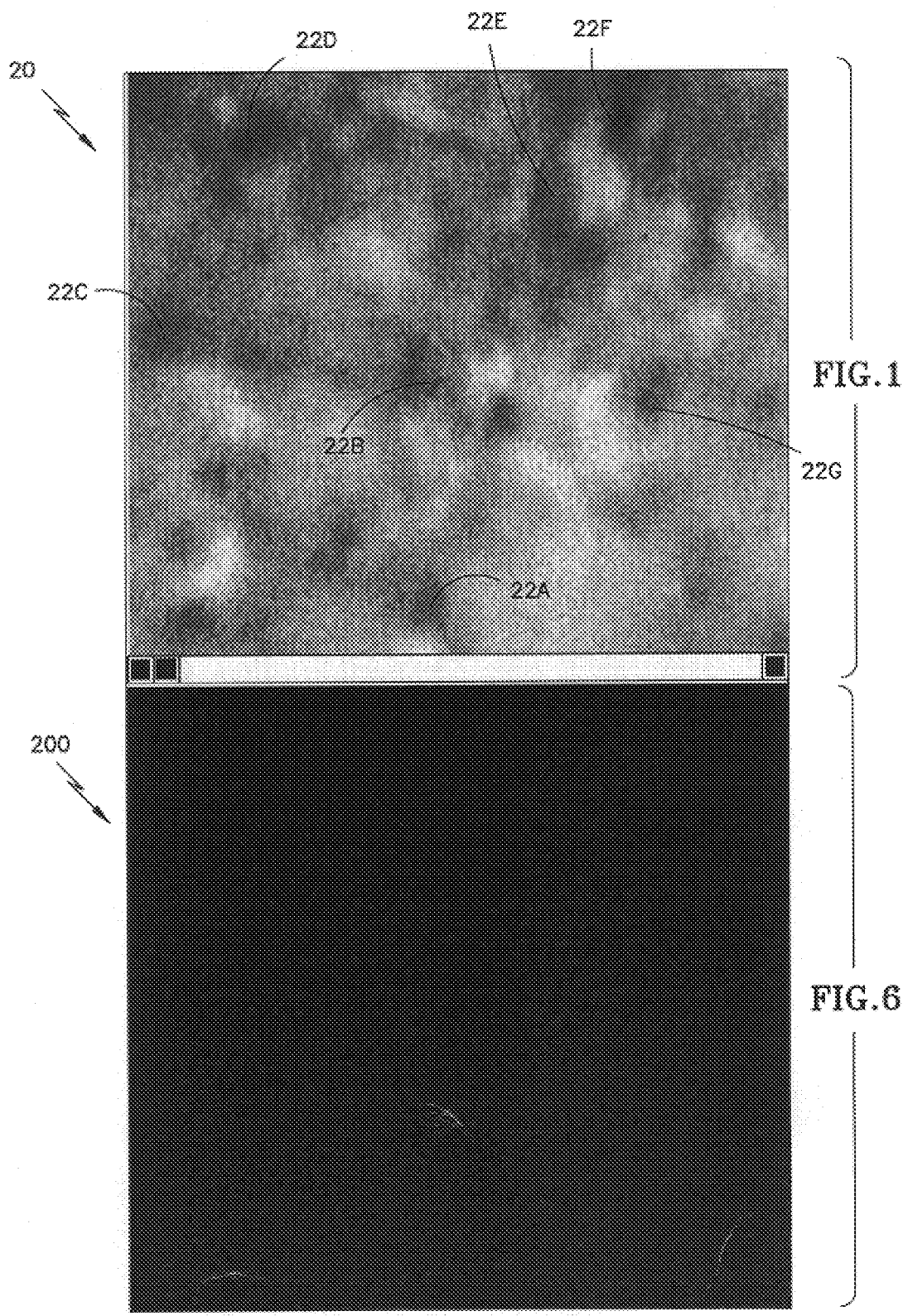
FIG. 1 is an x-ray image of a first object having a relatively large grain microstructure.

Referring now to FIG. 6, an image 200 is indicative of an output signal generated by the inspection system 30 in response to the x-ray image 20 (FIG. 1). The absence of any relatively light regions in the image 200 indicates that there are no indications of the image 20 that indicate a significant defect in the first object.

Referring now to FIG. 7, an image 300 is indicative of an output signal generated by the inspection system 30 in response to the x-ray image 25 (FIG. 2). The image 300 has one relatively light region, thereby identifying the one region 26G (FIG. 2) in the image 25 that is indicative of a significant defect in the second object.

Referring now to FIG. 8, a radiographic image 400 of another object (not shown) having relatively large, generally randomly oriented grains has a high level of intensity variations. The intensity variations make it difficult to determine the presence or absence of relatively subtle but significant defects based on simple inspection of the image. Note that a particularly dark region 402 represents air adjacent to the side of the object.

Referring now to FIG. 9, an image 450 is indicative of an output signal generated by the inspection system 30 in response to the x-ray image 400 (FIG. 8). Side by side comparison of the two images 400, 450 suggests that the inspection system 30 determined most of the intensity variation of the image 400 to be distortion. A relatively lighter region identifies one region in the image 400 that is not indicative of distortion but rather is indicative of a relatively subtle yet significant defect in the object.

Figures 10, 11:
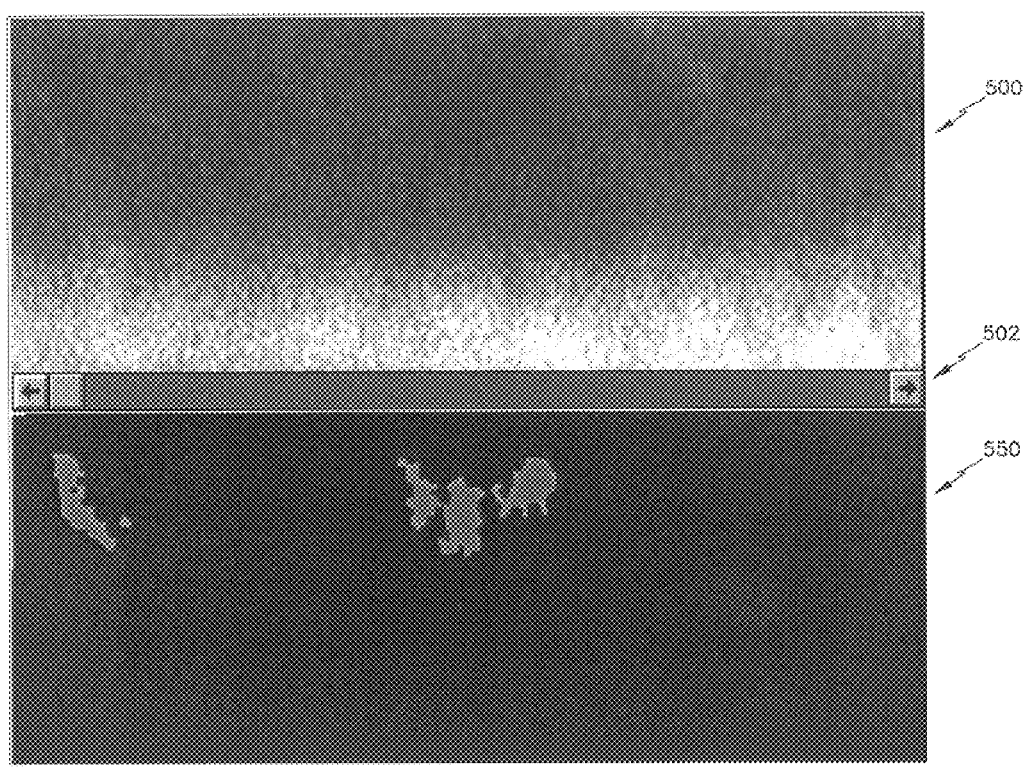
FIG. 10 is an x-ray image of another object to be inspected by the inspection system of FIG. 3.
FIG. 11 is an output image produced by the inspection system of FIG. 3 in response to the x-ray image of FIG. 10.

Referring now to FIG. 10, a radiographic image 500 of another object (not shown) having relatively large, generally randomly oriented grains has a high level of intensity variations. The intensity variations make it difficult to determine the presence or absence of relatively subtle but significant defects based on simple inspection of the image. Note that a particularly light region 502 represents a change in thickness but not a defect.

Referring now to FIG. 11, an image 550 is indicative of an output signal generated by the inspection system 30 in response to the x-ray image 500 (FIG. 10). Side by side comparison of the two images 500, 550 suggests that the inspection system 30 determined most of the intensity variation of the image 500 (FIG. 10) to be distortion. However, relatively lighter regions in the image 550 identify regions in the image 500 that are not indicative of distortion but rather are indicative of relatively subtle yet significant defects in the object.

While the present invention has been described with reference to a best mode embodiment, this description is not meant to be construed in a limiting sense. For example, although the best mode embodiment discloses a centralized processor comprising a general purpose industrial computer 98, an image processor 99, a motion controller 100, and a program in memory, the processor 86 is not limited to such. The processor 86 may be distributed throughout the inspection system 30. A program may be stored in any type of storage media, inside or outside of the processor 86. Furthermore, the processor 86 may comprise additional portions and/or features. For example, if an analog x-ray detector is used then the image processor may further comprise a digitizer. Or, the processor 86 may comprise less than all the portions described above. For example, some embodiments may not require a dedicated image processor and/or a dedicated motion controller. Moreover, although the processor 86 in the best mode embodiment provides control signals to the manipulator 84, this aspect is not a requirement. Some embodiments may not require the processor 86 to command relative positioning of the object, the x-ray source 60 and the x-ray detector 62. Rather, positioning may be achieved manually or automatically without processor 86 intervention.

Moreover, those skilled in the art will recognize that although the processor 86 in the disclosed embodiment comprises programmed hardware, i.e. executed in software by a computer, it may take other forms, including hardwired hardware configurations, hardware manufactured in integrated circuit form, firmware, and combinations thereof. It should be understood that although the disclosed embodiment comprises a digital system with periodically sampled signals, the present invention may also be embodied in an analog system with continuous signals, or a combination of digital and analog systems.

There are various possible embodiments for providing a relative positioning of the object, the x-ray source 60, and the x-ray detector 62. In one embodiment, the motion controller 100 directs the manipulator 84 to move the object to a desired position and the processor 86 waits for a signal from the motion controller 100 indicating completion of the positioning of the object. The processor 86 then acquires and begins to process an image for that position while the motion controller 100 directs the manipulator 84 to move the object to the next desired position. After processing the image, the processor 86 waits for a signal from the motion controller 100 indicating the object is at the next desired position. The processor 86 then acquires and begins to process an image for that position. In another embodiment, the manipulator 84 moves the object, relative to the x-ray source 60 and/or the x-ray detector 62, at a substantially constant rate and direction and the image processor 99 processes the inspection signals at particular time intervals. The processor 86 calculates a change in position using the magnitude of the rate, e.g., provided to the processor 86 in advance, and the magnitude of the time interval.

The change in the position of the object relative to the x-ray detector 62 is preferably accomplished by translating the object relative to the x-ray detector 62, more preferably translating parallel to one or more of the detector reference axes, axis $X_d$ and axis $Y_d$. The change in the relative positioning preferably results in a translation of the image of the object. For example, if the objected is to be displaced, the displacement of the object should comprise more than just moving the object closer or further from the x-ray detector 62. Different relative positioning between the object, the x-ray source 60 and/or the x-ray detector 62 may also be achieved by translating the x-ray detector 62, or by positioning x-ray detectors at different positions, and combinations thereof. This is preferably achieved by translation but rotation or combinations could also achieve it thereof. If the object is not to be positioned, inspection systems typically translate the source and detector concurrently to maintain alignment to the source signal.

Generally, in an x-ray system, the further the x-ray source 60 is from the object, the larger the spot size can be. Thus, various x-ray sources may be employed depending upon physical limitations and geometric magnification requirements. Some embodiments may use an amorphous silicon digital detector to achieve enhanced resolution and image uniformity. An alternative embodiment of the x-ray detector 62 comprises an image intensifier, a condensing lens, and a video camera.

Although described above with respect to a best mode embodiment for determining correlation between the x-ray images, any measure of correlation may be used. In some embodiments, it may not be necessary to identify the blobs in each of the x-ray images. Further, the determination may involve pixel shifting the x-ray image by an amount corresponding to the relative positional change, followed by an AND operation, to thereby retain those indications of the x-ray image that are consistent with the change in positional relationship (real features) and remove other features (e.g. grain diffraction noise, electrical noise) from the output image signal.

Although the present invention is described with respect to inspection of the critical areas and/or substantially all of the diffuser case, the present invention is not limited to such. At least in regard to x-ray inspection, the present invention is typically used on objects of at least three square inches in area, the size of an ordinary turbine airfoil.

The present invention is not limited to x-ray inspection systems but rather may be used in any inspection system that employs a source 60 and a formed or a direct image from a detector 62. The source signal 64 may be an electromagnetic or acoustic ( e.g., ultrasonic) wave or energy, and may be directed or non-directed, i.e., propagating. For example, it is apparent that the present invention may be easily extended to ultrasonic inspections to remove the effects of distortion in the signal due to grain scattering, thereby improving defect sensitivity. The inspection signals need not be indicative of density of an object but rather need only be indicative of at least one internal physical characteristic of an object. Indications in the inspection signals need not be indicative of a density defect but rather may be indicative of any physical characteristic associated with any measure of the at least one physical characteristic of the object.

It is understood that various modifications of the above embodiments, as well as additional embodiments of the invention, will be apparent to persons skilled in the art upon reference to this description, without departing from the spirit of the invention, as recited in the claims appended hereto. It is therefore contemplated that the appended claims will cover any such modifications or embodiments as fall within the true scope of the invention.

What is claimed is:

1. A method for use in inspecting an object, the method comprising the steps of:

generating a plurality of inspection signals each indicative of at least one internal physical characteristic of a portion of the object;

changing orientation for generating each of the plurality of inspection signals, wherein for each of the plurality of inspection signals the step of generating includes the steps of:

directing a source signal at the portion of the object;

detecting an output signal from the portion of the object, the output signal being indicative of the at least one internal physical characteristic of the portion of the object, the step of directing and the step of detecting being performed using an orientation relative to the portion of the object; and generating the inspection signal in response to the output signal; and generating, in response to the plurality of inspection signals, a signal indicative of at least one measure of correlation between the plurality of inspection signals to reduce effects of distortion on the results of the inspection for better distinguishing between distortion and defects in inspected objects.

2. The method of claim 1 wherein the object is at least three square inches in area.

3. The method of claim 1 wherein the output signals from the portion of the object are transmitted through the portion of the object.

4. The method of claim 1 wherein the step of detecting comprises detecting with a detector having a plurality of detector elements disposed generally within a plane, and the different orientations used in generating the plurality of inspection signals are provided by translating at least one of the detector and the object in a direction parallel to the plane.

5. The method of claim 1 wherein the plurality of inspection signals comprises at least three inspection signals.

6. A method for use in inspecting an object, the method comprising the steps of:

generating a plurality of inspection signals each indicative of at least one internal physical characteristic of a portion of the object;

changing orientation for generating each of the plurality of inspection signals, wherein for each of the plurality of inspection signals the step of generating includes the steps of:

directing a source signal at the portion of the object;

detecting an output signal from the portion of the object, the output signal being indicative of the at least one internal physical characteristic of the portion of the object, the step of directing and the step of detecting being performed using an orientation relative to the portion of the object; and generating the inspection signal in response to the output signal; and generating, in response to the plurality of inspection signals, a signal indicative of at least one measure of correlation between the plurality of inspection signals;

wherein the step of generating the signal indicative of the at least one measure of correlation between the plurality of inspection signals comprises the steps of:

providing at least one reference indicative of at least one measure of the at least one internal physical characteristic;

determining for each of the plurality of inspection signals, and in response to the at least one reference, no less than zero indications of the inspection signal indicating at least one physical characteristic associated with the at least one measure of the at least one internal physical characteristic; and generating, in response thereto, the signal indicative of the at least one measure of correlation between the plurality of inspection signals.

7. The method of claim 6 wherein the step of generating the signal indicative of the at least one measure of correlation between the plurality of inspection signals further comprises the steps of:

determining for each of the plurality of inspection signals, a position and a size of at least one of the no less than zero indications;

comparing the position and the size of the at least one of the no less than zero indications of at least one of the plurality of inspection signals with the position and the size of the at least one of the no less than zero indications of at least one other of the plurality of inspection signals; and generating, in response thereto, the signal indicative of the at least one measure of correlation between the plurality of inspection signals.

8. The method of claim 7 wherein the object is at least three square inches in area, the output signals from the portion of the object are transmitted through the portion of the object, the step of detecting comprises detecting with a detector having a plurality of detector elements disposed generally within a plane, and the different orientations used in generating the plurality of inspection signals are provided by translating at least one of the detector and the object in a direction parallel to the plane.

9. A method for use in inspecting an object, the method comprising the steps of:

generating a plurality of inspection signals each indicative of at least one internal physical characteristic of a portion of the object;

changing orientation for generating each of the plurality of inspection signals, wherein for each of the plurality of inspection signals the step of generating includes the steps of:

directing a source signal at the portion of the object;

detecting an output signal from the portion of the object, the output signal being indicative of the at least one internal physical characteristic of the portion of the object, the step of directing and the step of detecting being performed using an orientation relative to the portion of the object; and generating the inspection signal in response to the output signal; and generating, in response to the plurality of inspection signals, a signal indicative of at least one measure of correlation between the plurality of inspection signals;

wherein the step of generating the signal indicative of the at least one measure of correlation between the plurality of inspection signals comprises the steps of:

providing at least one reference indicative of at least one density associated with at least one defect;

determining for each of the plurality of inspection signals, and in response to the at least one reference, no less than zero indications of the inspection signal indicating at least one density associated with the at least one defect; and generating, in response thereto, the signal indicative of the at least one measure of correlation between the plurality of inspection signals.

10. The method of claim 9 wherein the step of generating the signal indicative of the at least one measure of correlation between the plurality of inspection signals further comprises the steps of determining for each of the plurality of inspection signals, a position and a size of at least one of the no less than zero indications;

comparing the position and the size of the at least one of the no less than zero indications of at least one of the plurality of inspection signals with the position and the size of the at least one of the no less than zero indications of at least one other of the plurality of inspection signals; and generating, in response thereto, the signal indicative of the at least one measure of correlation between the plurality of inspection signals.

11. The method of claim 10 wherein the object is at least three square inches in area, the output signals from the portion of the object are transmitted through the portion of the object, the step of detecting comprises detecting with a detector having a plurality of detector elements disposed generally within a plane, and the different orientations used in generating the plurality of inspection signals are provided by translating at least one of the detector and the object in a direction parallel to the plane, and further comprising the step of using the method to inspect.

12. An apparatus for use in an inspection system to inspect an object, the inspection system having a source and a detector, the apparatus comprising:

means for providing a plurality of orientations of the source and the detector relative to a portion of the object, each of the plurality of orientations being different than the others of the plurality of orientations, wherein at each of the plurality of orientations the source provides a source signal directed at the portion of the object and the detector detects an output signal from the portion of the object, the output signal being indicative of at least one internal physical characteristic of the portion of the object, and the detector generates, in response to the output signal, one of a plurality of inspection signal indicative of the at least one internal physical characteristic of the portion of the object; and means for generating, in response to the plurality of inspection signals, a signal indicative of at least one measure of correlation between the plurality of inspection signals to reduce effects of distortion on the results of the inspection for better distinguishing between distortion and defects in inspected objects.

13. The apparatus of claim 12 wherein the means for providing a plurality of orientations includes means for positioning the object between the source and the detector.

14. The apparatus of claim 12 wherein the plurality of inspection signals comprises at least three inspection signals.

15. An apparatus for use in an inspection system to inspect an object, the inspection system having a source and a detector, the apparatus comprising:

means for providing a plurality of orientations of the source and the detector relative to a portion of the object, each of the plurality of orientations being different than the others of the plurality of orientations, wherein at each of the plurality of orientations the source provides a source signal directed at the portion of the object and the detector detects an output signal from the portion of the object, the output signal being indicative of at least one internal physical characteristic of the portion of the object, and the detector generates, in response to the output signal, one of a plurality of inspection signal indicative of the at least one internal physical characteristic of the portion of the object; and means for generating, in response to the plurality of inspection signals, a signal indicative of at least one measure of correlation between the plurality of inspection signals;

wherein the means for generating the signal indicative of the at least one measure of correlation between the plurality of inspection signals comprises:

means for providing at least one reference indicative of at least one measure of the at least one internal physical characteristic; and means for determining for each of the plurality of inspection signals, and in response to the at least one reference, no less than zero indications of the inspection signal indicating at least one physical characteristic associated with the at least one measure of the at least one internal physical characteristic; and means for generating, in response thereto, the signal indicative of the at least one measure of correlation between the plurality of inspection signals.

16. The apparatus of claim 15 wherein the means for generating the signal indicative of the at least one measure of correlation between the plurality of inspection signals further comprises:

means for determining for each of the plurality of inspection signals, a position and a size of at least one of the no less than zero indications;

means for comparing the position and the size of the at least one of the no less than zero indications of at least one of the plurality of inspection signals with the position and the size of the at least one of the no less than zero indications of at least one other of the plurality of inspection signals; and means for generating, in response thereto, the signal indicative of the at least one measure of correlation between plurality of inspection signals.

17. The apparatus of claim 16 wherein the means for providing a plurality of orientations includes means for positioning the object between the source and the detector, the detector has a plurality of detector elements disposed generally within a plane, and the means for providing a plurality of different orientations includes means for translating at least one of the detector and the object in a direction parallel to the plane.

18. An apparatus for use in an inspection system to inspect an object, the inspection system having a source and a detector, the apparatus comprising:

means for providing a plurality of orientations of the source and the detector relative to a portion of the object, each of the plurality of orientations being different than the others of the plurality of orientations, wherein at each of the plurality of orientations the source provides a source signal directed at the portion of the object and the detector detects an output signal from the portion of the object, the output signal being indicative of at least one internal physical characteristic of the portion of the object, and the detector generates, in response to the output signal, one of a plurality of inspection signal indicative of the at least one internal physical characteristic of the portion of the object; and means for generating, in response to the plurality of inspection signals, a signal indicative of at least one measure of correlation between the plurality of inspection signals;

wherein the means for generating the signal indicative of the at least one measure of correlation between the plurality of inspection signals comprises:

means for providing at least one reference indicative of at least one density associated with at least one defect;

means for determining for each of the plurality of inspection signals, and in response to the at least one reference, no less than zero indications of the inspection signal indicating at least one density associated with the at least one defect; and means for generating, in response thereto, the signal indicative of the at least one measure of correlation between the plurality of inspection signals.

19. The apparatus of claim 18 wherein the means for generating the signal indicative of the at least one measure of correlation between the plurality of inspection signals further comprises:

means for determining for each of the plurality of inspection signals, a position and a size of at least one of the no less than zero indications;

means for comparing the position and the size of the at least one of the no less than zero indications of at least one of the plurality of inspection signals with the position and the size of the at least one of the no less than zero indications of at least one other of the plurality of inspection signals; and means for generating, in response thereto, the signal indicative of the at least one measure of correlation between the indications provided by the plurality of inspection signals.

20. The apparatus of claim 19 wherein the means for providing a plurality of orientations includes means for positioning the object between the source and the detector, the detector has a plurality of detector elements disposed generally within a plane, and the means for providing a plurality of different orientations includes means for translating at least one of the detector and the object in a direction parallel to the plane.

* * * * *